United States Patent
Takasugi (10) Patent No.: US 11,921,111 B2
(45) Date of Patent: Mar. 5, 2024

(54) MAGNETIC SENSOR, DETECTION DEVICE AND DETECTION SYSTEM

(71) Applicant: TDK Corporation, Tokyo (JP)

(72) Inventor: Keisuke Takasugi, Tokyo (JP)

(73) Assignee: TDK Corporation, Tokyo (JP)

(*) Notice: Subject to any disclaimer, the term of this patent is extended or adjusted under 35 U.S.C. 154(b) by 1060 days.

(21) Appl. No.: 16/787,182

(22) Filed: Feb. 11, 2020

(65) Prior Publication Data
US 2020/0300848 A1  Sep. 24, 2020

(30) Foreign Application Priority Data

Mar. 20, 2019 (JP) .................. 2019-052347
Dec. 23, 2019 (JP) .................. 2019-231051

(51) Int. Cl.
*G01R 33/09* (2006.01)
*G01N 15/06* (2006.01)
*G01N 33/543* (2006.01)

(52) U.S. Cl.
CPC ... *G01N 33/54326* (2013.01); *G01N 15/0606* (2013.01); *G01N 15/0656* (2013.01); *G01R 33/093* (2013.01)

(58) Field of Classification Search
CPC ......... G01N 33/54326; G01N 15/0656; G01N 15/0606; G01R 33/093
See application file for complete search history.

(56) References Cited

U.S. PATENT DOCUMENTS

| 7,906,345 B2 | 3/2011 | Wang et al. |
| 8,367,805 B2 | 2/2013 | Chamberlain et al. |
| 9,151,763 B2 | 10/2015 | Osterfeld et al. |

(Continued)

FOREIGN PATENT DOCUMENTS

| JP | 2011-221017 A | 11/2011 |
| JP | 5161459 B2 | 12/2012 |

(Continued)

OTHER PUBLICATIONS

Chinese Office Action dated Jul. 22, 2022 in corresponding Chinese Patent Application No. 202010079081.4 (English translation only).

(Continued)

*Primary Examiner* — Alesa Allgood
(74) *Attorney, Agent, or Firm* — POSZ LAW GROUP, PLC (57) ABSTRACT

A magnetic sensor used to detect detection substances in samples includes a substrate having a first surface and a second surface, which is opposite to the first surface, a magnetoresistance effect element, which is provided on the first surface and in which the resistance of the magnetoresistance effect element changes in accordance with an input magnetic field, and a protective layer that covers the magnetoresistance effect element. The magnetoresistance effect element is configured in a line shape extending in a first direction on the first surface, and has a first region that is positioned at the outer periphery in a plan view, and a second region that is surrounded by the first region. The height of a top surface of the protective layer on the first region is greater than the height of a top surface of the protective layer on the second region.

11 Claims, 8 Drawing Sheets

(56) References Cited

U.S. PATENT DOCUMENTS

| | | |
|---|---|---|
| 2018/0299407 A1 | 10/2018 | Haratani et al. |
| 2019/0113479 A1* | 4/2019 | Tsuboike ............. G01R 33/098 |
| 2019/0128882 A1 | 5/2019 | Haratani et al. |

FOREIGN PATENT DOCUMENTS

| | | |
|---|---|---|
| JP | 6043395 B2 | 11/2016 |
| JP | 6101215 B2 | 3/2017 |
| WO | 2017/082227 A1 | 5/2017 |
| WO | 2017170238 A1 | 10/2017 |
| WO | WO-2017170238 A1 * | 10/2017 ........... C12Q 1/6825 |

OTHER PUBLICATIONS

Japanese Office Action dated Jan. 19, 2021 in corresponding JP Application No. 2019-231051 (English Machine Translation provided).

* cited by examiner

MAGNETIC SENSOR, DETECTION DEVICE AND DETECTION SYSTEM

The present application is based on Japanese Patent Application No. 2019-052347 filed on Mar. 20, 2019 and Japanese Patent Application No. 2019-231051 filed on Dec. 23, 2019, the disclosures of which are incorporated herein by reference.

TECHNICAL FIELD

The present invention relates to a magnetic sensor, a detection device and a detection system.

BACKGROUND

As a quantitative immunoassay, radio immunoassay (RIA; immunoradiometric assay (IRMA)) is known. In this method, it is possible to label competitive antigens or antibodies and to quantitatively measure antigens from measurement results of specific radioactivity, through radio-nuclides. Immunoassaying is a method of labeling target objects such as antigens or the like and accomplishing indirect measurement. This method is highly sensitive and thus makes significant contributions in clinical diagnoses but has the drawback that it is necessary to ensure the safety of the radionuclides and thus designated facilities and devices are necessary. Hence, as a method that is easier to use, a method using a biosensor that uses magnetic beads or the like as indicators has been proposed (see Patent Literature 1~4).

A conventional biosensor includes a substrate, a magnetoresistance effect element such as a GMR element or the like, provided on the substrate, and a protective film that covers the magnetoresistance effect element. After magnetic beads having an affinity for biomolecules in samples are captured in a protective layer via the biomolecules, a magnetic field is applied, and then a stray magnetic field is generated from the magnetic beads. The resistance value of the magnetoresistance effect element changes due to this stray magnetic field being input into the magnetoresistance effect element, and it is possible to indirectly detect the biomolecules based on the resistance value change.

RELATED LITERATURE

Patent Literature

[PATENT LITERATURE 1] Japanese patent 5161459
[PATENT LITERATURE 2] Japanese patent 6043395
[PATENT LITERATURE 3] Japanese patent 6101215
[PATENT LITERATURE 4] International release 2017/82227 pamphlet

OVERVIEW OF THE INVENTION

Problem to be Solved by the Invention

The magnetoresistance effect element in the above-described biosensor is produced by forming, on a substrate, a magnetoresistance effect film having a layered configuration in which a nonmagnetic film is interposed between two ferromagnetic films, and patterning the magnetoresistance effect film using a resist pattern as a mask. At the outer periphery of the magnetoresistance effect element produced in this manner, the magnetization of the ferromagnetic layer (free layer) becomes unstable. Consequently, when magnetic beads are captured in the protective layer on a prescribed region that includes the outer periphery of the magnetoresistance effect element and a stray magnetic field generated from the magnetic beads is applied on the magnetoresistance effect element in which the magnetization of the ferromagnetic layer (free layer) is unstable, noise is superimposed on the output from the biosensor. As a result, there is a problem that biomolecule detection accuracy declines.

In consideration of the foregoing, it is an object of the present invention to provide a magnetic sensor including a magnetoresistance effect element, which can detect detection substances with high accuracy using magnetic beads, a detection device and a detection system.

Means for Solving the Problem

In order to resolve the above-described problem, the present invention provides a magnetic sensor used to detect detection substances in samples. The magnetic sensor includes a substrate, which has a first surface and a second surface opposite to the first surface, a magnetoresistance effect element, which is provided on the first surface of the substrate and in which the resistance of the magnetoresistance effect element changes in accordance with an input magnetic field, and a protective layer that covers the magnetoresistance effect element. The magnetoresistance effect element is configured in a line shape extending in a first direction on the first surface of the substrate, and has a first region that is positioned at the outer periphery in a planar view, and a second region that is surrounded by the first region. The height of a top surface of the protective layer on the first region of the magnetoresistance effect element is greater than the height of a top surface of the protective layer on the second region of the magnetoresistance effect element.

The height to the top surface of the protective layer from a top surface of the magnetoresistance effect element in the first region of the magnetoresistance effect element may be 40 nm or greater. The first region of the magnetoresistance effect element may be a region that is at least 40 nm from an edge of the top surface of the magnetoresistance effect element in the inward direction, orthogonal to the edge.

In the outer periphery region of the magnetoresistance effect element, a height adjustment layer may be provided between the magnetoresistance effect element and the protective layer. Lead electrodes electrically connected to each of the two ends of the magnetoresistance effect element in the lengthwise direction are further provided. The height adjustment layer may be configured by the same material as the lead electrodes or may be configured by an insulating material.

The height of the outer periphery region of the magnetoresistance effect element may be greater than the height of the inner region of the magnetoresistance effect element. A GMR element can be used as the magnetoresistance effect element.

EFFICACY OF THE INVENTION

With the present invention, it is possible to provide a magnetic sensor provided with a magnetoresistance effect element capable of detecting detection substance with high accuracy using magnetic beads, a detection device and a detection system.

BEST MODE FOR IMPLEMENTING THE INVENTION

Embodiments of the present invention will be described with reference to the drawings. In the present embodiment, a biosensor used to detect biomolecules as detection substances will be described as an example of a magnetic sensor, but the present invention is not limited to this embodiment. The detection substances that can be detected by the magnetic sensor may include various organic compounds such as volatile organic compounds (VOCs) contained in contaminated water, in addition to biomolecules.

Figure 1:
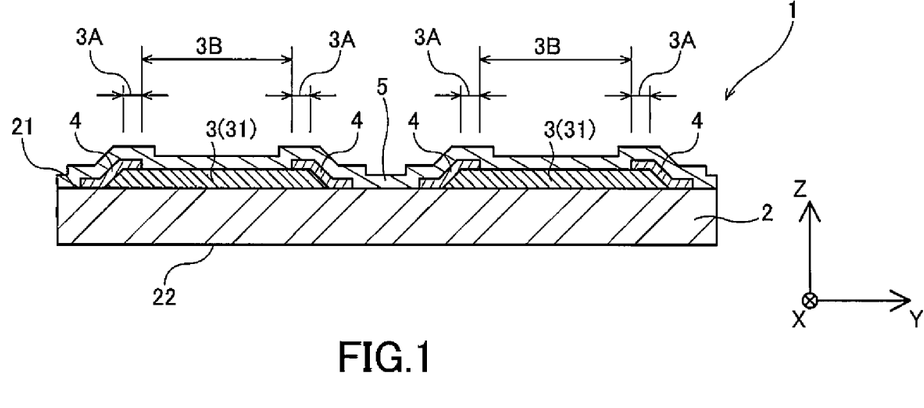
FIG. 1 is a cross-sectional end view showing the schematic configuration of a biosensor according to an embodiment of the present invention.
Figure 2:
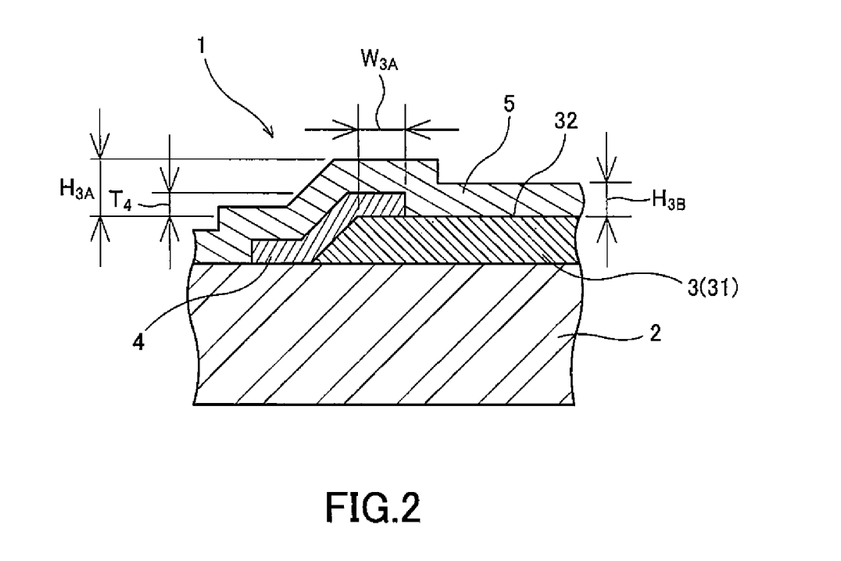
FIG. 2 is a partial enlarged cross-sectional end view showing the schematic configuration of a biosensor according to an embodiment of the present invention.
Figure 3:
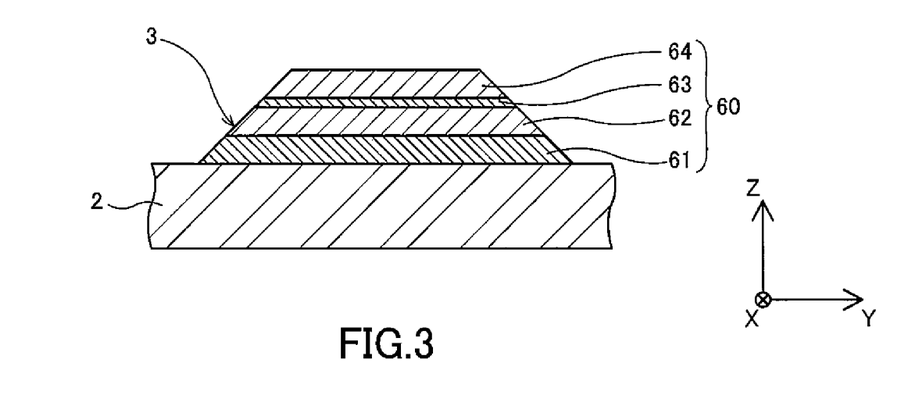
FIG. 3 is a cross-sectional end view showing the schematic configuration of a magnetoresistance effect element according to an embodiment of the present invention.
Figure 4:
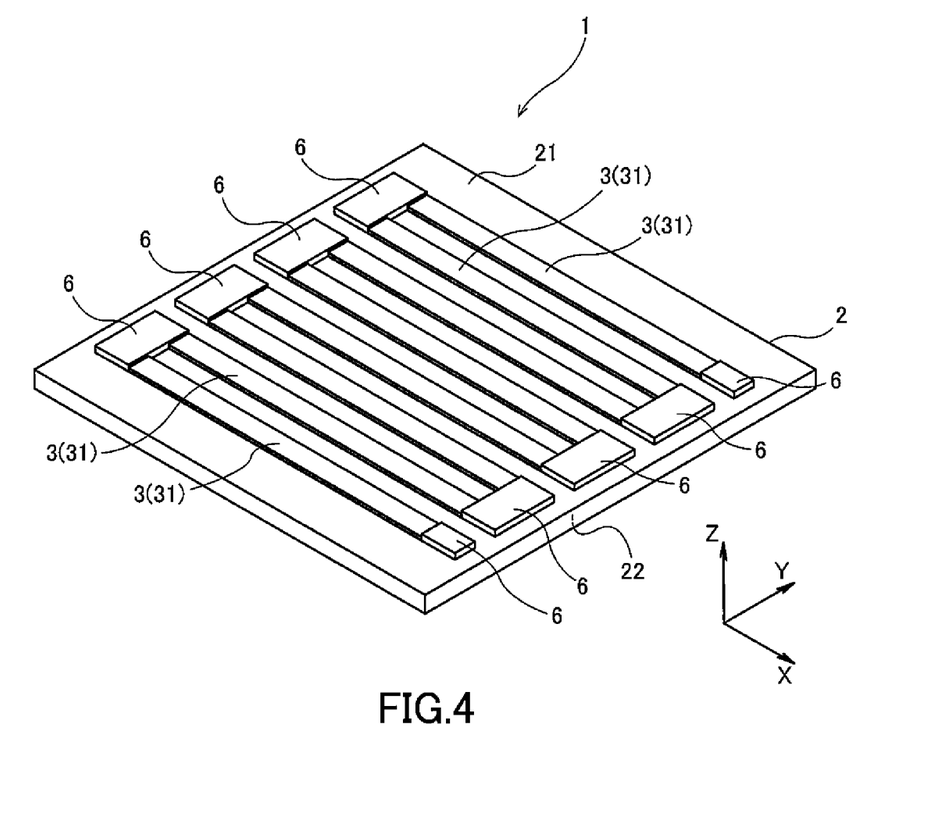
FIG. 4 is a perspective view showing the schematic configuration of a biosensor according to an embodiment of the present invention.

FIG. 1 is a cross-sectional end view showing the schematic configuration of a biosensor according to this embodiment, FIG. 2 is a partial enlarged cross-sectional end view showing the schematic configuration of the biosensor according to this embodiment, FIG. 3 is a cross-sectional end view showing the schematic configuration of a magnetoresistance effect element according to this embodiment, and FIG. 4 is a perspective view showing the schematic configuration of a biosensor according to this embodiment.

In a biosensor according to this embodiment, the "X-axis direction, Y-axis direction and Z-axis direction" are stipulated in a number of the drawings, as necessary. Here, the X-axis direction and the Y-axis direction are directions orthogonal to each other within the plane of the substrate in this embodiment (within a plane substantially parallel to a first surface and a second surface of the substrate), and the Z-axis direction is the direction of thickness of the substrate (the direction orthogonal to the first surface and the second surface of the substrate).

A biosensor 1 according to this embodiment includes a substrate 2 having a first surface 21 and a second surface 22 opposite to the first surface 21, a magnetoresistance effect element 3 provided on the first surface 21 of the substrate 2, a height adjustment layer 4 positioned on a first region 3A positioned at the outer periphery of the magnetoresistance effect element 3, and a protective layer 5 that covers the top of the magnetoresistance effect element 3. In the biosensor 1 according to this embodiment, by applying a magnetic field H on magnetic beads 10 with biomolecules in a sample, which is captured in the protective layer 5 on the magnetoresistance effect element 3, and by detecting a stray magnetic field HS from the magnetic beads 10 with the magnetoresistance effect element 3, it is possible to detect the biomolecules.

The substrate 2 may be a rectangular one on which the magnetoresistance element 3 can be mounted, and, for example, it can be a semiconductor substrate such as a silicon wafer or the like, a ceramic substrate such as an AlTiC substrate, an alumina substrate or the like, a resin substrate, or a glass substrate or the like. An underlayer (omitted from the drawings) that includes Al2O3 may be provided on the first surface 21 of the substrate 2, in particular, between the first surface 21 of the substrate 2 and the magnetoresistance effect element 3, in accordance with the type of the substrate 2. The thickness of the substrate 2 can be appropriately set from the perspective of the strength of the substrate 2 and thinning and weight reductions of the biosensor 1, but it may be on the order of 5~100 nm, for example.

In this embodiment, a spin valve type of GMR element or the like can be used as the magnetoresistance effect element 3. The magnetoresistance effect element 3 has an MR layered body 60 that includes an antiferromagnetic layer 61, a magnetization fixed layer 62, a nonmagnetic layer 63 and a free layer 64 layered in that order from the substrate 2 side (see FIG. 3). The antiferromagnetic layer 61 is configured by an antiferromagnetic material and serves the role of fixing the direction of magnetization of the magnetization fixed layer 62 by causing exchange coupling with the magnetization fixed layer 62. The magnetoresistance effect element 3 may have a configuration in which the free layer 64, the nonmagnetic layer 63, the magnetization fixed layer 62 and the antiferromagnetic layer 64 are layered in that order from the substrate 2 side. In addition, the antiferromagnetic layer 61 may be omitted by the magnetization fixed layer 62 having a layered ferri structure of a ferromagnetic layer/nonmagnetic intermediate layer/ferromagnetic layer and being a self-pinned fixed layer (Synthetic Ferri Pinned layer, or SFP layer) in which both ferromagnetic layers are antiferromagnetically coupled.

In a GMR element as the magnetoresistance effect element 3, the nonmagnetic layer 63 is a nonmagnetic electroconductive layer. In a GMR element, the resistance value changes in accordance with the angle formed by the direction of magnetization of the free layer 64 with respect to the direction of magnetization of the magnetization fixed layer 62. The resistance value is minimized when this angle is 0° (when the magnetization directions are parallel to each other), and the resistance value is maximized when this angle is 180° (when the magnetization directions are antiparallel to each other).

The magnetoresistance effect element 3 is configured in a meandering shape in which a plurality of line-shaped sections 31 extending in the X-axis direction (first direction) is aligned in the Y-axis direction (second direction) and the ends of adjacent line-shaped sections 31 are connected by lead electrodes 6 (see FIG. 4). In FIG. 4, depictions of the height adjustment layer 4 and the protective layer 5 are omitted because the drawing becomes complicated.

A GMR element as the magnetoresistance effect element 3, in general, has a relatively low element resistance value, so in order to cause a signal of prescribed strength to be output from the biosensor 1, it is necessary to make the linewidth of the GMR element narrow and the line length long. Furthermore, by forming the GMR element in the above-described meandering shape, it is possible to make the linewidth of the GMR element narrow and the line length long within a limited region on the first surface 21 of the substrate 2. The lead electrode 6 may be configured by one type of electroconductive material out of Cu, Al, Au, Ta, Ti or the like, for example, or may be configured by a combination film of two or more types of electroconductive materials.

In the magnetoresistance effect element 3 configured by the above-described plurality of line-shaped sections 31, the magnetization direction of the magnetization fixed layer 62 is substantially parallel to the short direction of each line-shaped section 31. In the biosensor 1 according to this embodiment, by applying a magnetic field H in a direction orthogonal to the first surface 21 of the substrate 2 on the magnetic beads 10 captured in the protective layer 5 on the magnetoresistance effect element 3, a stray magnetic field HS is generated from the magnetic beads 10 and applied on the magnetoresistance effect element 3 (see FIG. 5). Since this stray magnetic field HS is applied on the magnetoresistance effect element 3, the direction of magnetization of the free layer 64 changes, and through this the resistance value of the magnetoresistance effect element 3 changes. Since this change in resistance value is output as a signal, the existence and abundance of biomolecules in the sample can be detected in the biosensor 1.

The length of the line-shaped sections 31 in the lengthwise direction can be appropriately set in accordance with the size of the biosensor 1 as a whole and the sensitivity or the like required of the biosensor 1, but, for example, it may be on the order of 10~500 μm, and the length in the short direction may be on the order of 0.2~10 μm, for example.

In a plan view of the biosensor 1 according to this embodiment, each line-shaped section 31 of the magnetoresistance effect element 3 has a first region 3A positioned at the outer periphery of each of the line-shaped sections 31, and a second region 3B positioned inside the first region 3A surrounded by the first region 3A. The first region 3A is a region with a predetermined width W3A facing toward the inside orthogonal to each of the edges, from each of the edges of the top surface 32 of each of the line-shaped sections 31. This width W3A is preferably 40 nm or more. As described below, since the height adjustment layer 4 is provided on the first region 3A of the magnetoresistance effect element 3, the top surface of the protective layer 5 in the first region 3A can be taller than the top surface of the protective layer 5 in the second region 3B. More specifically, the height H3A of the top surface of the protective layer 5 in the first region 3A is preferably 40 nm or more. This means that when magnetic beads 10 exist in the region within a radius of 40 nm from the edges of the top surface of the magnetoresistance effect element 3, noise is readily superimposed on the output of the biosensor 1. Consequently, when the width W3A of the first region 3A is less than 40 nm, there is a worry that noise could be easily superimposed on the output from the biosensor 1 by the stray magnetic field HS from the magnetic beads 10 captured near the first region 3A in the second region 3B. The upper limit of the width W3A of the first region 3A may be less than one-half the width in the short direction of the top surface of each of the line-shaped sections 31 of the magnetoresistance effect element 3, and preferably on the order of 10% of the width in the short direction.

In the biosensor 1 according to this embodiment, the height adjustment layer 4 is provided in the first region 3A of the magnetoresistance effect element 3. Since the height adjustment layer 4 is provided, it is possible to make the height of the top surface of the protective layer 5 in the first region 3A higher than the top surface of the protective layer 5 in the second region 3B. Because both ends in the lengthwise direction of the plurality of line-shaped sections 31 configuring the magnetoresistance effect element 3 are covered by the lead electrodes 6, the height adjustment layer 4 may be provided in the first region 3A of both ends in the dotted direction of the plurality of line-shaped sections 31. In this case, the lead electrodes 6 that cover both ends in the lengthwise direction of each of the line-shaped sections 31 also serve the role of functioning as the height adjustment layer 4.

The height adjustment layer 4 is, for example, configured by the same material as the lead electrodes 6 or may be configured by an insulating material such as $SiO_2$, $Al_2O_3$, $Si_3N_4$, TiN, TaN, TaO, TiO, MN or the like.

The thickness T4 of the height adjustment layer 4 is appropriately set such that noise is not superimposed on the output from the biosensor 1 by the stray magnetic field HS of the magnetic beads 10 captured in the protective layer 5 on the first region 3A of the magnetoresistance effect element 3. As described below, if the height H3A of the top surface of the protective layer 5 in the first region 3A is 40 nm or greater, noise is unlikely to be superimposed on the output from the biosensor 1, and it is possible to detect biomolecules with high accuracy using the magnetic beads 10. Consequently, for example, when the thickness T5 of the protective layer 5 is on the order of 30 nm, the thickness T4 of the height adjustment layer 4 may be 10 nm or greater.

Figure 6:
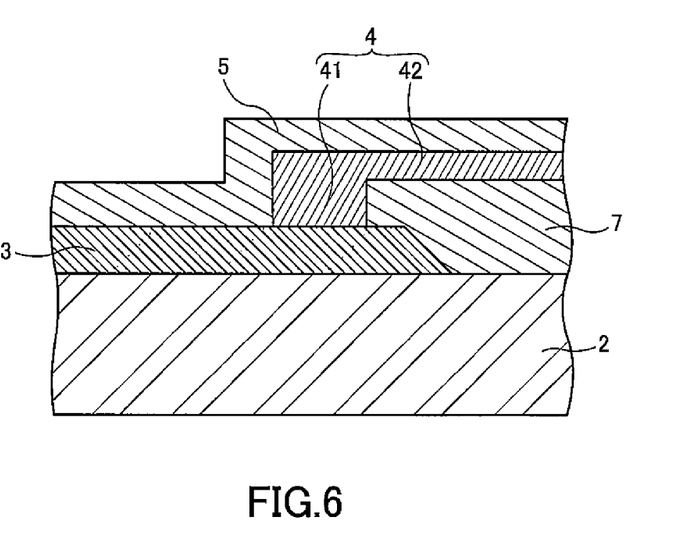
FIG. 6 is a partial enlarged cross-sectional end view showing the schematic configuration of another aspect (first) of a height adjustment layer in an embodiment of the present invention.
Figure 7:
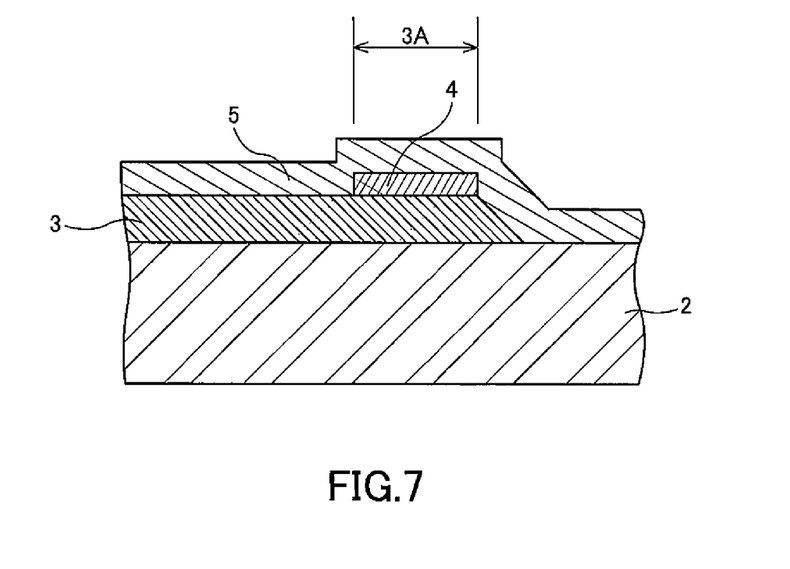
FIG. 7 is a partial enlarged cross-sectional end view showing the schematic configuration of another aspect (second) of a height adjustment layer in an embodiment of the present invention.
Figure 8:
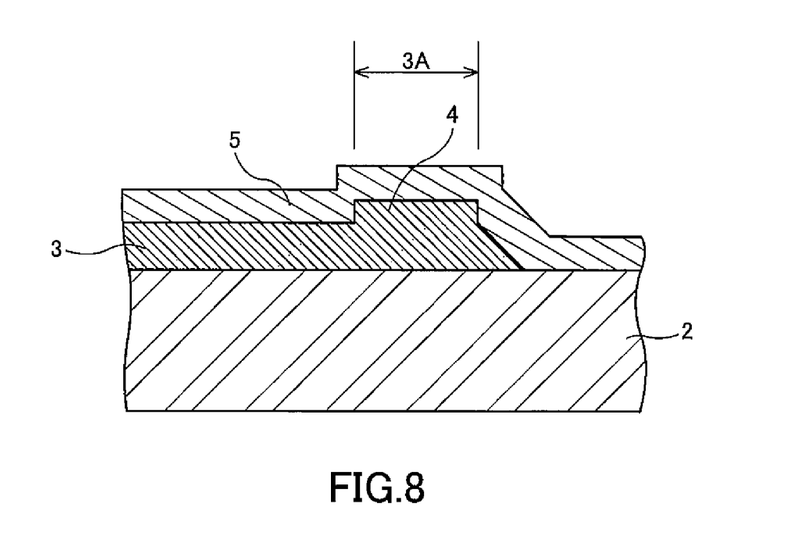
FIG. 8 is a partial enlarged cross-sectional end view showing the schematic configuration of another aspect (third) of a height adjustment layer in an embodiment of the present invention.

The shape of the height adjustment layer 4 is not particularly limited as long as it is possible to make the height of the top surface of the protective layer 5 in the first region 3A of the magnetoresistance effect element 3 greater than the height of the top surface of the protective surface 5 in the second region 3B. For example, the height adjustment layer 4 may be provided to reach the first surface 21 of the substrate 2 from the first region 3A of the magnetoresistance effect element 3 (see FIG. 1), or may have a base section 41 established upward from the top surface of the magnetoresistance effect element 3 in the first region 3A and an extension section 42 extending toward the outside of the magnetoresistance effect element 3 along the in-plane direction from the base section 41, with an insulating layer 7 provided between the extension section 42 and the magnetoresistance effect element 3 (see FIG. 6), or may be provided only on the upper surface of the magnetoresistance effect element 3 in the first region 3A (see FIG. 7). In addition, the height adjustment layer 4 may be configured by the same material as the magnetoresistance effect element 3 (see FIG. 8). In the aspect shown in FIG. 8, the height adjustment layer 4 should be formed by reattaching the material by which the milled MR film 70 is configured on the top surface of the magnetoresistance effect element 3 in the first region 3A, in the milling process of the MR film 70 in the manufacturing procedures for the biosensor 1.

In this embodiment, the protective layer 5 that covers the entirety of the first surface 21 of the substrate 2, the magnetoresistance effect element 3 and the height adjustment layer 4 is a layer in which biomolecules accumulated in the magnetic beads 10 can be captured. The biomolecules accumulated in the magnetic beads 10 are captured in the protective layer 5 though an electrostatic interaction, a hydrogen bonding interaction or the like with the protective layer 5. Consequently, the protective layer 5 may be configured by a material that can exert an electrostatic interaction, a hydrogen bonding interaction or the like with a biomolecule of SiO2, Al2O3, Si3N4, TiN, TaN, TaO, TiO, AlN or the like, for example. In order to make it possible to easily capture biomolecules in the surface of the protective layer 5, in particular, in the surface of the protective layer 5 on the second region 3B of the magnetoresistance effect element 3, a material with an affinity capable of bonding specifically with the biomolecules that are the target of detection may be provided.

The thickness T5 of the protective layer 5 may be such that the stray magnetic field HS generated from the magnetic beads 10 bonded with the biomolecules captured in the top surface of the protective layer 5 in the second region 3B can be applied on the magnetoresistance effect element 3, and can be appropriately set in accordance with the thickness T4 of the height adjustment layer 4 so that the height H3A of the of the top surface of the protective layer 5 in the first region 3A (the height from the top surface of the magnetoresistance effect element 3) is at least 40 nm, while the height H3B of the top surface of the protective layer 5 in the second region 3B (the height from the top surface of the magnetoresistance effect element 3) is on the order of 30 nm. For example, when the thickness T4 of the height adjustment layer 4 is on the order of 10 nm, the thickness T5 of the protective layer 5 can be set to around 30 nm, for example.

Since the biosensor 1 having the above-described composition contacts with a sample including the biomolecules 11 that are the detection target, it is possible to capture these biomolecules 11 in the surface of the protective layer 5. Furthermore, after the biomolecules 11 captured in the surface of the protective layer 5 and the magnetic beads 10 have been caused to bond, the magnetic beads 10 and the biomolecules 11 captured in the surface of the protective layer 5 on the first region 3A of the magnetoresistance effect element are selectively removed by a gradient magnetic field or cleaning or the like. In this embodiment, since the height of the surface of the protective layer 5 on the first region 3A of the magnetoresistance effect element 3 is greater than the height of the surface of the protective layer 5 on the second region 3B, the surface flow velocity of the cleaning fluid is larger than on the protective layer 5 in the second region 3B, cleaning is readily promoted and the magnetic beads 10 detached by the gradient magnetic field or the like readily collide. As a result, it is possible to easily and selectively remove the magnetic beads 10 and the biomolecules 11 captured in the surface of the protective layer 5 on the first region 3A of the magnetoresistance effect element 3 by the gradient magnetic field or cleaning or the like.

Figure 5:
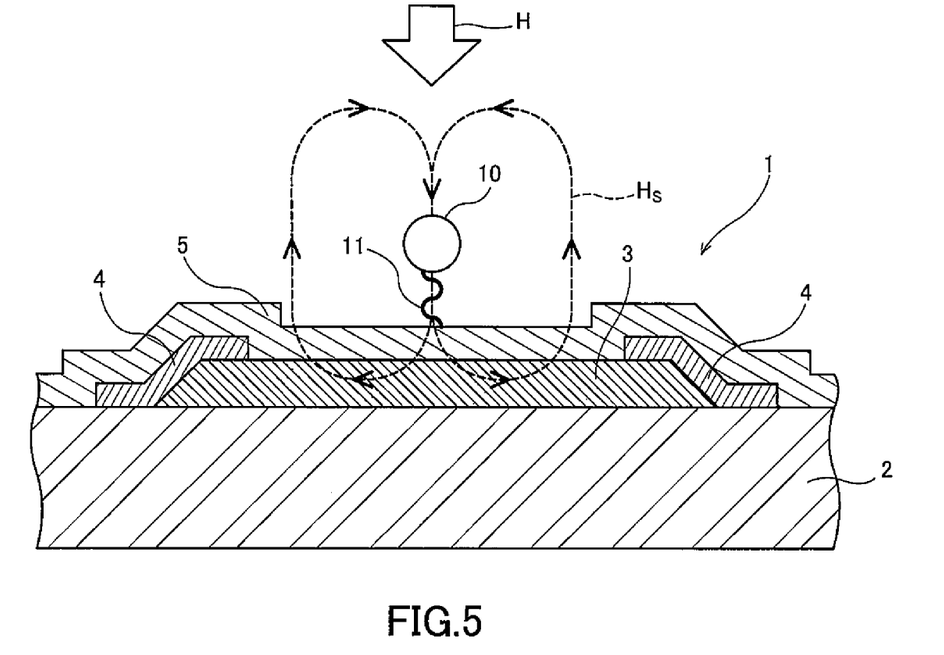
FIG. 5 is a cross-sectional end view for describing an overview of the biomolecule detection method used in the biosensor according to an embodiment of the present invention.

As described above, after the biomolecules 11 and the magnetic beads 10 are left in the surface of the protective layer 5 on the second region 3B of the magnetoresistance effect element 3, by applying a magnetic field H in a direction orthogonal to the first surface 21 of the substrate 2, the magnetic beads 10 are magnetized, and the stray magnetic field HS is generated from the magnetic beads 10 (see FIG. 5). Since this stray magnetic field HS is applied on the magnetoresistance effect element 3, the magnetization direction of the free layer 64 changes, and as a result the resistance value of the magnetoresistance effect element 3 changes. This resistance value change has a correlation (linear correlation) with the number of magnetic beads 10 bonded to the biomolecules 11 captured in the surface of the protective layer 5, so this resistance value change is output from the biosensor 1 as a signal, and it is possible to detect the presence and the abundance of biomolecules that are the detection target in the sample.

As the biomolecules 11 that can be detected using the biosensor 1 according to this embodiment, the following can be listed, for example: nucleic acids such as DNA, mRNA, miRNA, siRNA, artificial nucleic acids (for example, Locked Nucleic Acid (LNA), Bridged Nucleic Acid (BNA) or the like) or the like (these may be naturally derived or chemically synthesized); peptides such as ligands, cytokines, hormones or the like; proteins such as receptors, enzymes, antigens, antibodies or the like; or cells, viruses, bacteria, fungi or the like.

In addition, as samples containing the biomolecules 11 that are the detection target, the following can be listed, for example: blood, blood serum, blood plasma, urine, puffy coat, saliva, semen, chest exudate, cerebrospinal fluid, tears, phlegm, mucus, lymph, abdominal fluid, pleural effusion, amniotic fluid, bladder lavage fluid, bronchoalveolar lavage fluid, cell extract fluid, cell culture supernatants and the like.

The magnetic beads may be particles that can be magnetized, and, for example, may be particles or the like configured by gold, iron oxide or the like. The average particle diameter of the magnetic beads 10 may be on the order of 5~250 nm, for example, and preferably on the order of 20~150 μm. The average particle diameter of the magnetic beads 10 can, for example, be measured using a laser diffraction-type particle diameter distribution measurement device (product name: SALD-2300, made by Shimadzu Corp.).

The surface of the magnetic beads 10 may be fixed to a protein such as streptavidin or the like and may be further provided with an affinity substance capable of bonding specifically with the biomolecules. When used to capture ligands as the biomolecules 11, the magnetic beads 10 preferably have a hydrophilic surface, and when used to capture antibodies as the biomolecules 11, the magnetic beads 10 preferably have a hydrophobic surface.

With the biosensor 1 having the above-described configuration, by providing the height adjustment layer 4 on the first region 3A of the magnetoresistance effect element 3, it is possible to make it difficult to capture the magnetic beads 10 on the first region 3A, or it is possible to make it difficult for the stray magnetic field HS from the magnetic beads 10 captured on the first region 3A to have an effect on the resistance value change of the magnetoresistance effect element 3. Consequently, it is possible to detect the biomolecules with high accuracy using the magnetic beads 10, without superimposing noise on the output signal from the biosensor 1.

The biosensor 1 having the above-described configuration can, for example, be produced as follows. FIGS. 9A-9F are process flow diagrams showing the procedures of the method of manufacturing the biosensor 1 in cross-sectional end views according to this embodiment.

An underlayer (omitted from drawings) that includes Al2O3 or the like is formed on a planned region that forms the magnetoresistance effect element 3 on the first surface 21 of the substrate 2, which is a semiconductor substrate such as a silicon wafer or the like, a ceramic substrate such as an AlTiC substrate, an alumina substrate or the like; a resin substrate; or a glass substrate or the like. The MR film 70 (a layered film with an antiferromagnetic film, a ferromagnetic film, a nonmagnetic film and a ferromagnetic film layered in that order) is formed through sputtering or the like on the first surface 21 of the substrate 2 (see FIG. 9A).

Figure 9A:
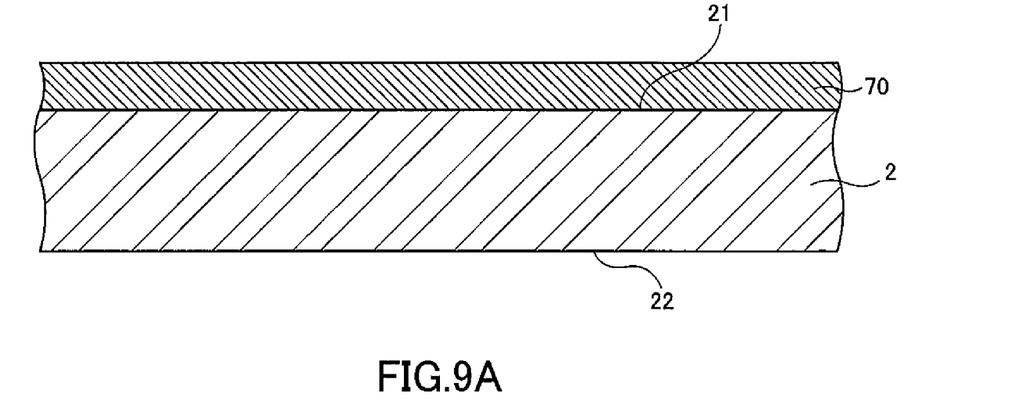
FIG. 9A is a cross-sectional end view showing one procedure out of the manufacturing procedures for the biosensor according to an embodiment of the present invention.
Figure 9B:
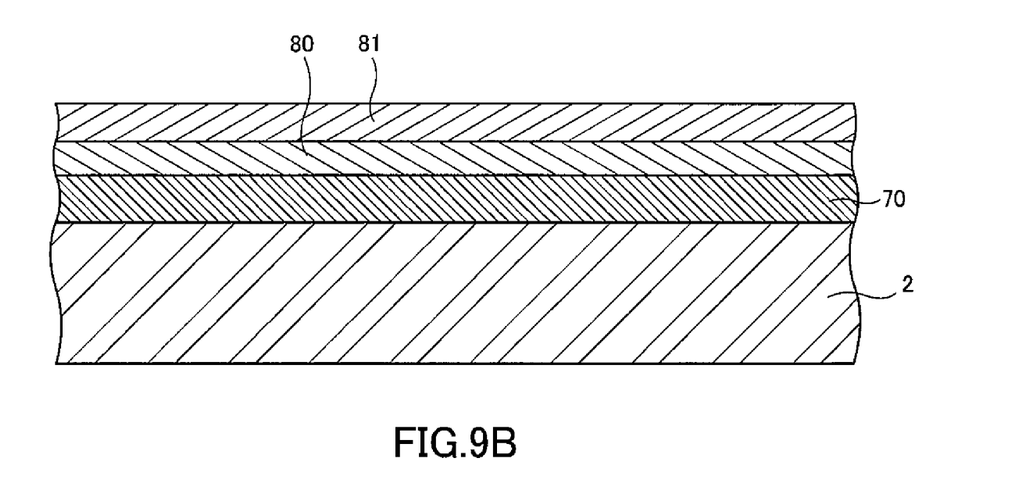
FIG. 9B is a cross-sectional end view showing the procedure following the procedure shown in FIG. 9A.

Next, a first resist layer 80 and a second resist layer 81 covering the MR film 70 are layered in this order (see FIG. 9B). Through an exposure/development process, a resist pattern 84 having the layered structure of a first resist pattern 82 and a second resist pattern 83 is formed, corresponding to the magnetoresistance effect element 3 (see FIG. 9C).

Figure 9C:
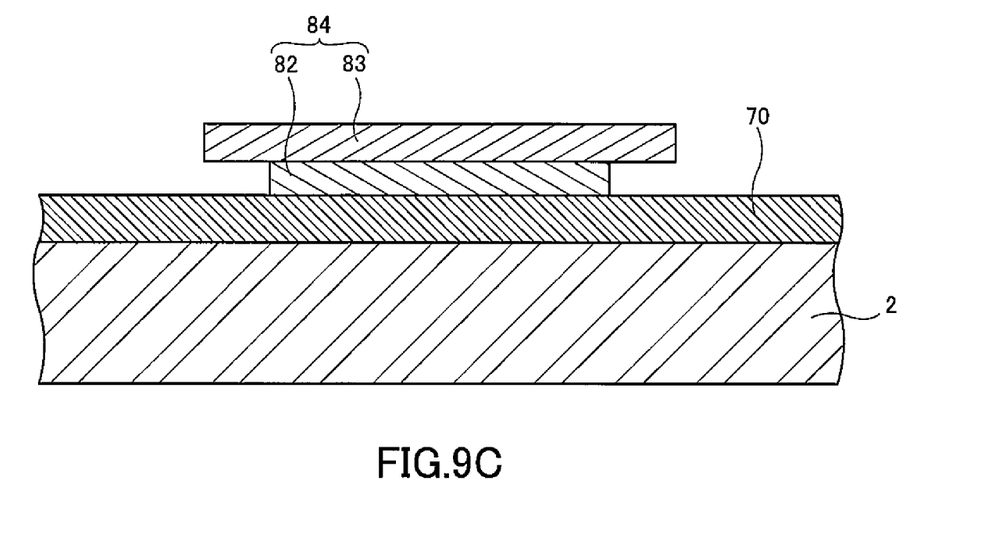
FIG. 9C is a cross-sectional end view showing the procedure following the procedure shown in FIG. 9B.

As the resist material that configures the first resist layer 80 and the second resist layer 81, a positive type or a negative type may be used, but preferably the resist material that configures the first resist layer 80 (for example, cyclopentanone-class) has a lower resistance to the developing fluid (for example, an organic alkali developing fluid such as tetramethylammonium hydroxide (TMAH) or the like) than the resist material that configures the second resist layer 81 (for example, Novolac resin-class). Through this, when developing the first resist layer 80 and the second resist layer 81 simultaneously, the side surface of the first resist pattern 82 is eroded, and a space SP is formed that is surrounded by the MR film 70, the side surface of the first resist pattern 82 and the bottom surface of the second resist pattern 83. By the space SP formed in this manner, it is possible to stipulate the region where the below-described height adjustment layer 4, that is, the first region 3A, is stipulated. By the amount of erosion of the first resist layer 80 in the in-plane direction, the width W3A of the first region 3A is controlled, but the amount of erosion can be controlled by appropriately setting the exposure conditions and the like, for example.

Figure 9D:
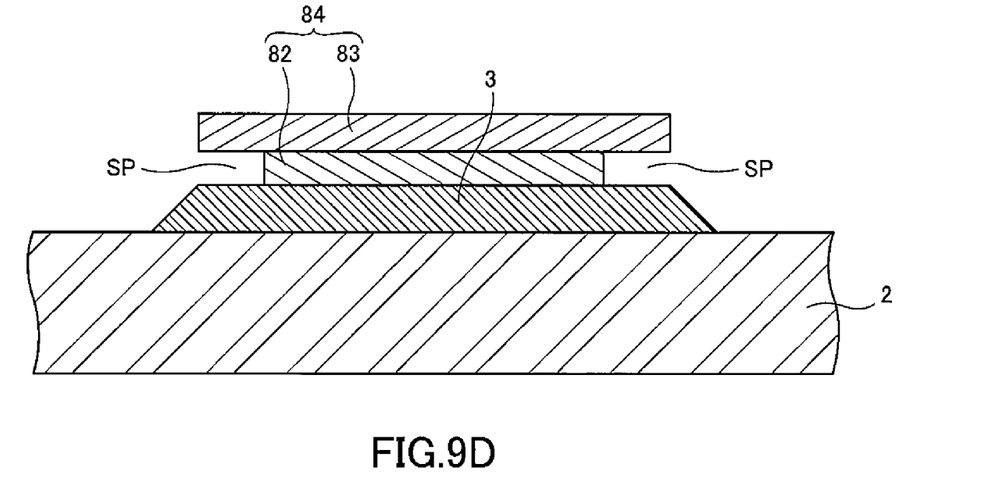
FIG. 9D is a cross-sectional end view showing the procedure following the procedure shown in FIG. 9C.

Next, after milling the MR film 70 using the resist pattern 84 as a mask, by applying a magnetic field while implementing a prescribed annealing process, the plurality of line-shaped sections 31 of the magnetoresistance effect element 3 is formed on the first surface of the substrate 2 (see FIG. 9D). The applied magnetic field can be appropriately set so that a prescribed exchange magnetic anisotropy is induced between the antiferromagnetic layer 61 and the magnetization fixed layer 62 in accordance with the effective vertical magnetic anisotropic energy Keff of the like given from the vertical magnetic anisotropic energy Ku and the shape anisotropic energy Kd of the magnetization fixed layer 62, the constituent materials of each layer and the film thickness, dimensions and shape of each layer of the magnetoresistance effect element 3.

Figure 9E:
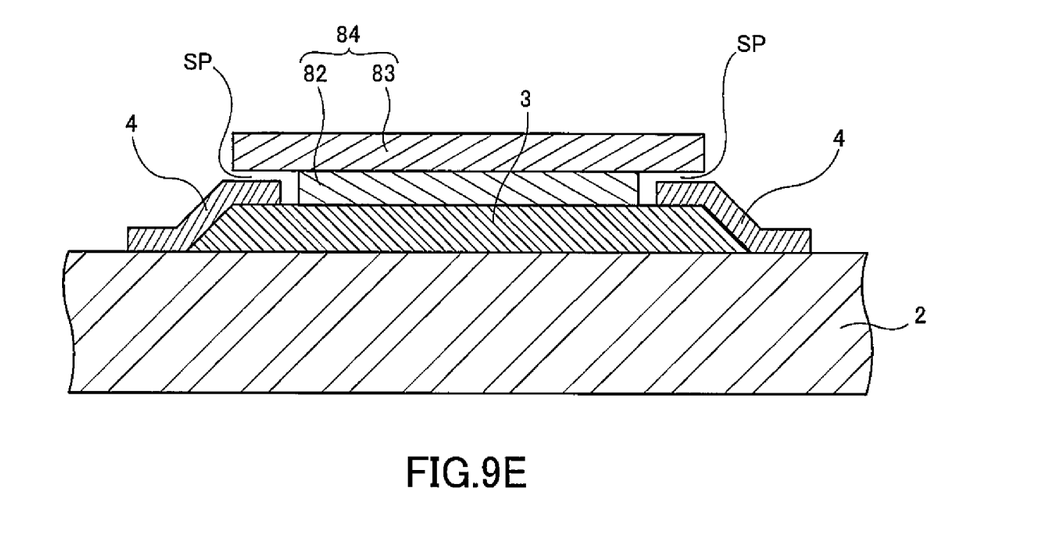
FIG. 9E is a cross-sectional end view showing the procedure following the procedure shown in FIG. 9D.

Next, in addition to forming the lead electrodes 6 that continues the ends of adjacent line-shaped sections 31 in the lengthwise direction through sputtering of electroconductive materials or the like, the height adjustment layer 4 is formed on the first region 3A of each line-shaped section 31 (see FIG. 9E). As described above, a resist pattern 84 having a layered structure of the first resist pattern 82 and the second resist pattern 83 is formed on the top surface of the line-shaped sections 31, and a space SP is formed on a prescribed region facing inward from the edges of the top surface of the line-shaped sections 31 (see FIG. 9C). By having this kind of space SP, it is possible to stipulate the region (the first region 3A) where the height adjustment layer 4 is formed by the sputtering or the like of electroconductive materials. That is, it is possible to control the width W3A of the first region 3A and the thickness T4 of the height adjustment layer 4 formed on the first region 3A, by the size of the aforementioned space SP. Specifically, by adjusting the thickness and width (erosion amount) of the first resist pattern 82, the size of the aforementioned space SP is adjusted, and through this, it is possible to control the width W3A of the first region 3A and the thickness T4 of the height adjustment layer 4 formed on the first region 3A.

When the height adjustment layer 4 is configured by the same electroconductive material as the lead electrodes 6, the height adjustment layer 4 is formed by sputtering an electroconductive material on the first region 3A of each of the line-shaped sections 31 simultaneously with forming the lead electrodes 6. On the other hand, when the height adjustment layer 4 is configured by an insulating material, the height adjustment layer 4 can be formed by forming the insulating material on the first region 3A of each of the line-shaped sections 31 before or after forming the lead electrodes 6.

Figure 9F:
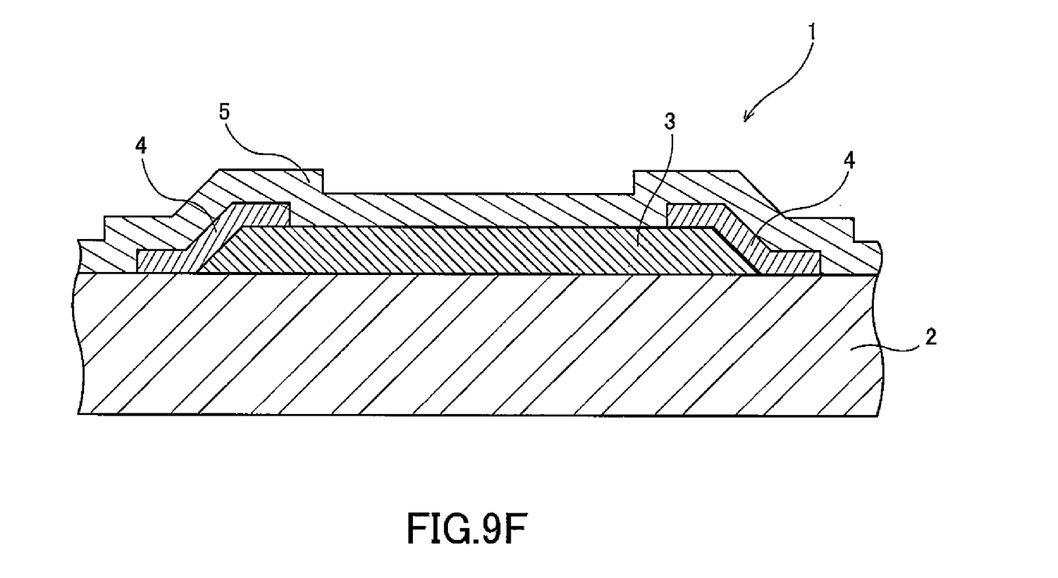
FIG. 9F is a cross-sectional end view showing the procedure following the procedure shown in FIG. 9E.

Finally, after removing the resist pattern 84, the protective layer 5 that covers the first surface 21 of the substrate 2, the magnetoresistance effect element 3 and the height adjustment layer 4 is formed (see FIG. 9F). Through this, the biosensor 1 according to this embodiment can be manufactured.

Figure 10:
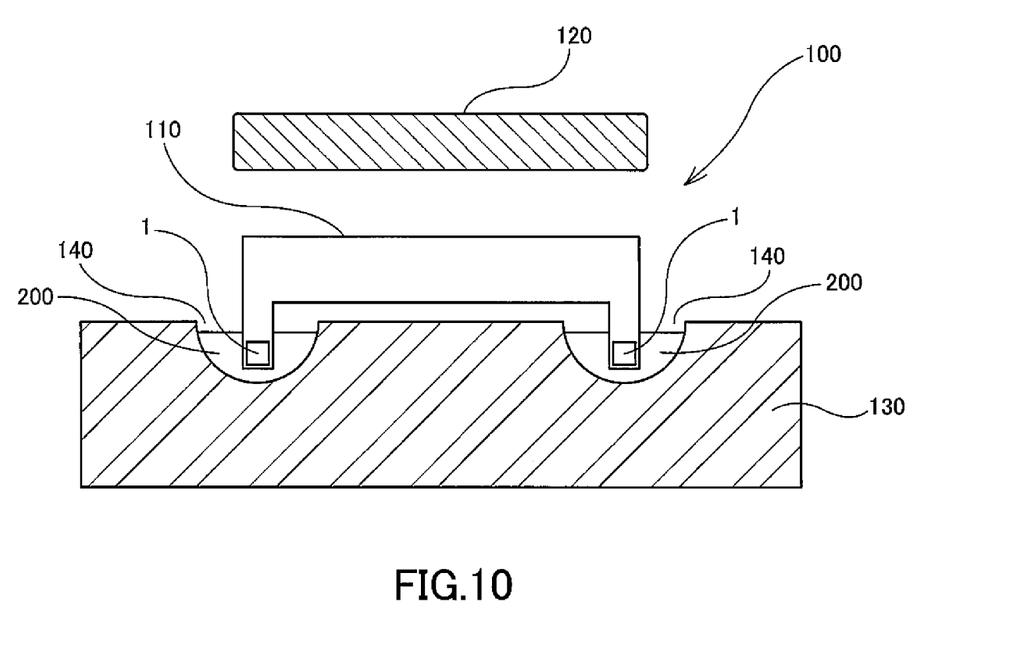
FIG. 10 is a cross-sectional end view showing the schematic configuration of a detection system according to an embodiment of the present invention.

A detection device using the biosensor 1 having the above-described configuration and a detection system provided with this detection device will be described. FIG. 10 is a cross-sectional end view showing the schematic configuration of a detection system according to this embodiment.

A detection system 100 in this embodiment is provided with a detection device having the biosensor 1 and a support unit 110 that supports this biosensor 1, a magnetic field generation unit 120 and a plate 130 having a plurality of reservoirs 140 that hold a sample 200 containing biomolecules.

A probe (for example, a ligand or the like) that can bond specifically with the biomolecules in the sample 200 may be provided on the surface of the protective layer 5 of the biosensor 1. Of course, the surface of the protective layer 5 of the biosensor 1 may also be configured so that the biomolecules are captured in the protective layer 5 by electrostatic interaction, hydrogen bonding interaction or the like, without the probe being provided on the surface of the protective layer 5 of the biosensor 1. The biomolecules in the sample 200 may be accumulated in the magnetic beads 10 (see FIG. 5). The support unit 110 that supports the biosensor 1 has a plurality of strip-shaped sections of a size capable of being inserted into each reservoir 140. When the tips of the strip-shaped sections are inserted into the reservoirs 140, the biosensor 1 is attached to the tip of each strip-shaped section so that the biosensor 1 is caused to contact the sample 200 housed in each reservoir 140. The support unit 110 is provided to be capable of raising and lowering, and through this, it is possible to insert each of the strip-shaped sections into each of the reservoirs 140 and to remove each from each of the reservoirs 140.

The magnetic field generation unit 120 is configured by coils or the like that can generate a magnetic field in a direction orthogonal to the first surface 21 of the substrate 2 of the biosensor 1, for example, and is provided so that a magnetic field can be applied on the biosensor 1 when the biosensor 1 is caused to contact the sample 200 housed in each reservoir 140.

In the detection system 100 having this kind of configuration, when the biosensor 1 is caused to contact the sample 200 housed in each of the reservoirs 140, the biomolecules accumulated in the magnetic beads 10 (see FIG. 5) are captured in the protective layer 5 of the biosensor 1. In this state, when a magnetic field is generated in a direction orthogonal to the first surface 21 of the substrate 2 from the magnetic field generation unit 120, the magnetic beads 10 are magnetized, and the stray magnetic field HS (see FIG. 5) is generated from the magnetic beads 10. Since this stray magnetic field HS is applied on the magnetoresistance effect element 3, the magnetization direction of the free layer 64 changes. As a result, the resistance value of the magnetoresistance effect element 3 changes, and a signal is output from the biosensor 1. The change in resistance value of the magnetoresistance effect element 3 has a correlation (linear correlation) with the number of magnetic beads 10 bonded to the biomolecules 11 captured in the surface of the protective layer 5, so in the detection system 100, the presence and abundance of the biomolecules in the sample can be detected based on the signal output from the biosensor 1.

In the above-described detection system 100, the magnetic field generation unit 120 causes a magnetic field to be generated in order to cause magnetization of the magnetic beads 10, and in a state in which the biomolecules accumulated in the magnetic beads 10 are captured in the protective layer 5 of the biosensor 1, an alternating current magnetic field may be caused to be generated in the in-plane direction (the in-plane direction of the XY plane) of the magnetoresistance effect element 3. In the detection system 100 of this aspect, first the biosensor 1 is caused to make contact with the sample 200 housed in each of the reservoirs 140, and the magnetic beads 10 are magnetized by the magnetic field generated from the magnetic field generation unit 120, and in addition, the biomolecules accumulated in the magnetized magnetic beads 10 are captured in the protective layer 5 of the biosensor 1. In this state, when the aforementioned alternating current magnetic field is caused to be generated from the magnetic field generation unit 120, the stray magnetic field is generated from the magnetic beads 10. Since this stray magnetic field is applied on the magnetoresistance effect element 3, the magnetization direction of the free layer 64 changes. As a result, the resistance value of the magnetoresistance effect element 3 changes, and a signal is output from the biosensor 1.

The embodiment described above was discussed in order to facilitate understanding of the present invention, and it is not intended to limit the present invention. Accordingly, each component disclosed in the above-described embodiment shall be construed to include all design modifications and equivalents that fall within the technical scope of the present invention.

In the above-described embodiment, after the electroconductive material (the same material as the lead electrodes 6) or the insulating material that configures the height adjustment layer 4 is formed as a film on the entire surface and the resist pattern is formed on the region corresponding to the first region 3A of the magnetoresistance effect element 3, the height adjustment layer 4 may be formed by an etching process using the resist pattern as a mask. The material that configures the MR film 70 may be reattached to the region corresponding to the first region 3A of the magnetoresistance effect element 3 by adjusting the exposure angle of the ion beam in the milling process of the MR film 70 using the resist pattern 84 as a mask, and through this the height adjustment layer 4 may be formed. In this case, the height of the height adjustment layer 4, that is the reattachment amount of the material that makes up the MR film 70, can be adjusted by the size of the space SP stipulated by the thickness and width (erosion amount) of the first resist pattern 82 and the exposure angle of the ion beam.

EMBODIMENT(S)

Below, the present invention will be described in greater detail by citing embodiments or the like, but the present invention is not limited to the below-described embodiments.

Test Example 1

The resistance change ratio (the change ratio taking as a standard the resistance value of the magnetoresistance effect element 3 prior to capture of the magnetic beads 10 (a zero magnetic field)) of the magnetoresistance effect element 3 in a state in which the magnetic beads 10 are captured in the first region 3A and the second region 3B was found through simulation for each different sample (samples 1~4) with the height H3B of the top surface of the protective layer 5 in the second region 3B of the biosensor 1 having the configuration shown in FIG. 1 being 30 nm and the height H3A of the top surface of the protective layer 5 in the first region 3A being as shown in Table 1. Results are shown in Table 1. Sample 4 is one with an aspect in which there is no height adjustment layer 4 in the biosensor 1 configured as shown in FIG. 1, that is, one in which the height H3A of the top surface of the protective layer 5 in the first region 3A and the height H3B of the top surface of the protective layer 5 in the second region 3B are the same. In addition, the resistance change ratio of each sample is a relative value when the designed value of the resistance change ratio of the magnetoresistance effect element 3 for obtaining the output sought from the biosensor 1 is taken to be 1.

TABLE 1

|  | H3A (nm) | Resistance change ratio |
| --- | --- | --- |
| Sample 1 | 60 | 0.99 |
| Sample 2 | 50 | 0.95 |
| Sample 3 | 40 | 0.93 |
| Sample 4 | 30 | 0.90 |

As is clear from the results shown in Table 1, when the biosensor 1 does not have a height adjustment layer 4 and the height H3A of the top surface of the protective layer 5 in the first region 3A and the height H3B of the top surface of the protective layer 5 in the second region 3B are the same (sample 4), the resistance change ratio of the magnetoresistance effect element 3 diverges from the ideal value, and noise is superimposed on the output of the biosensor 1. On this point, as shown in samples 1-3, by making the height H3A of the top surface of the protective layer 5 in the first region 3A higher than the height H3B of the top surface of the protective layer 5 in the second region 3B, it is possible to make the resistance change ratio of the magnetoresistance effect element 3 approach the ideal value. Furthermore, by having the height H3A of the top surface of the protective layer 5 in the first region 3A be 40 nm or greater, it is possible to reduce the effect of noise on the output of the biosensor 1, so it was confirmed that it is possible to detect the biomolecules 11 in the samples with high accuracy using the magnetic beads 10.

In addition, from the results shown in Table 1, it is possible to say that noise is readily superimposed on the output of the biosensor 1 when the magnetic beads 10 exist within a radius of 40 nm centered on the edge of the magnetoresistance effect element 3 in a cross-sectional view. Consequently, if the width W3A of the first region 3A is at least 40 nm from the edge of the magnetoresistance effect element 3, it is possible to say that the biomolecules 11 in the samples can be detected with high accuracy using the magnetic beads 10.

DESCRIPTION OF SYMBOLS

1—Biosensor
2—Substrate
21—First surface
22—Second surface
3—Magnetoresistance effect element
31—Line-shaped section
3A—First region
3B—Second region
4—Height adjustment layer
5—Protective layer

The invention claimed is:

1. A magnetic sensor used to detect detection substances in samples, the magnetic sensor comprising:
    a substrate which has a first surface and a second surface, which is opposite to the first surface;
    a magnetoresistance effect element, which is provided on the first surface of the substrate and in which a resistance of the magnetoresistance effect element changes in accordance with an input magnetic field; and
    a protective layer, which covers the magnetoresistance effect element;
    wherein the magnetoresistance effect element is configured in a line shape extending in a first direction on the first surface of the substrate, and has a first region that is positioned at the outer periphery, in a plan view, and a second region that is surrounded by the first region; and
    a height of a top surface of the protective layer on the first region of the magnetoresistance effect element is greater than a height of a top surface of the protective layer on the second region of the magnetoresistance effect element.

2. The magnetic sensor according to claim 1, wherein the height to the top surface of the protective layer from a top surface of the magnetoresistance effect element in the first region of the magnetoresistance effect element is 40 nm or greater.

3. The magnetic sensor according to claim 1, wherein the first region of the magnetoresistance effect element is a region that is at least 40 nm from an edge of a top surface of the magnetoresistance effect element in an inward direction, orthogonal to the edge.

4. The magnetic sensor according to claim 1, wherein in the first region of the magnetoresistance effect element, a height adjustment layer is provided between the magnetoresistance effect element and the protective layer.

5. The magnetic sensor according to claim 4, further comprising lead electrodes electrically connected to each of two ends of the magnetoresistance effect element in a lengthwise direction;
    wherein the height adjustment layer includes a first height adjustment layer, which is positioned in the first region at both ends of the magnetoresistance effect element in the lengthwise direction, and a second height adjustment layer, which is positioned in the first region at both ends of the magnetoresistance effect element in a short direction;
    the first height adjustment layer is configured by the lead electrodes; and
    the second height adjustment layer is configured by the same material as the lead electrodes.

6. The magnetic sensor according to claim 4, further comprising lead electrodes electrically connected to each of two ends of the magnetoresistance effect element in a lengthwise direction;
    wherein the height adjustment layer includes a first height adjustment layer, which is positioned in the first region at both ends of the magnetoresistance effect element in the lengthwise direction, and a second height adjustment layer, which is positioned in the first region at both ends of the magnetoresistance effect element in a short direction;
    the first height adjustment layer is configured by the lead electrodes; and
    the second height adjustment layer is configured by an insulating material.

7. The magnetic sensor according to claim 1, wherein a height of the first region of the magnetoresistance effect element is greater than a height of the second region of the magnetoresistance effect element.

8. The magnetic sensor according to claim 1, wherein the magnetoresistance effect element is a GMR element.

9. A detection device comprising:
    the magnetic sensor according to claim 1; and
    a support part that supports the magnetic sensor.

10. The detection device according to claim 9, wherein a probe capable of specifically bonding with the detection substances exists on the surface of the protective layer.

11. A detection system comprising:
    the detection device according to claim 9;
    a magnetic field generation part; and
    a holding part capable of holding the samples;
    wherein the detection device is provided so that the magnetic sensor can come into contact with the samples held in the holding part; and
    the magnetic field generation part is provided such that a magnetic field is applied on the magnetic sensor making contact with the samples held in the holding part.

* * * * *